United States Patent [19]

Smith

[11] Patent Number: 5,029,584
[45] Date of Patent: Jul. 9, 1991

[54] METHOD AND APPARATUS FOR MEASURING PATIENT BLOOD LOSS

[76] Inventor: Cornelius Smith, 110 Sleight St., Naperville, Ill. 60540

[21] Appl. No.: 410,544

[22] Filed: Sep. 21, 1989

[51] Int. Cl.$^5$ .......................... A61B 5/00; A61B 5/026
[52] U.S. Cl. ..................................... 128/638; 128/760; 604/27; 604/28; 604/43; 604/54; 356/39
[58] Field of Search .................. 128/637, 638, 760, 7; 604/27, 28, 39, 43, 54, 66, 67, 320, 325; 356/39, 40

[56] References Cited

U.S. PATENT DOCUMENTS

| | | | |
|---|---|---|---|
| 2,728,218 | 12/1955 | Ramser . | |
| 3,774,448 | 11/1973 | Gass et al. . | |
| 3,906,198 | 9/1975 | November . | |
| 4,227,814 | 10/1980 | Soodak et al. . | |
| 4,242,194 | 12/1980 | Steiner et al. | 356/39 |
| 4,243,883 | 1/1981 | Schwarzmann . | |
| 4,266,188 | 5/1981 | Thompson . | |
| 4,306,557 | 12/1981 | North | 604/119 |
| 4,357,105 | 11/1982 | Loretz | 356/40 |
| 4,417,585 | 11/1983 | Frank . | |
| 4,562,842 | 1/1986 | Morfeld et al. | 128/638 |
| 4,575,240 | 3/1986 | Hess et al. . | |
| 4,581,942 | 4/1986 | Ogura et al. . | |
| 4,726,381 | 2/1988 | Jones | 128/632 |
| 4,773,423 | 9/1988 | Hakky | 128/638 |
| 4,904,237 | 2/1990 | Janese | 604/28 |
| 4,911,549 | 3/1990 | Karkar | 356/39 |

Primary Examiner—Lee S. Cohen
Assistant Examiner—Krista M. Pfaffle
Attorney, Agent, or Firm—Allegretti & Witcoff, Ltd.

[57] ABSTRACT

The present invention is related to a method and apparatus for monitoring the cumulative amount of blood in a blood-containing liquid mixture emanating from a patient during a surgical procedure, or during recovery from a surgical procedure. The apparatus comprises a conduit for withdrawing a liquid mixture comprising blood from the surgical site. The liquid mixture is filtered, after which the blood concentration of the liquid mixture is measured by a first measuring means. The volumetric flow rate of the liquid mixture is also measured by a second measuring means. The liquid mixture blood concentration and flow rate readings are used to electronically calculate the cumulative amount of blood lost by the patient to the liquid mixture. Finally, the cumulative blood loss value is displayed. The liquid mixture is disposed of following the two measurements. A method of using such an apparatus during a surgical procedure and/or during recovery from a surgical procedure is also disclosed.

17 Claims, 1 Drawing Sheet

FILTER

DATA PROCESSING MEANS

METHOD AND APPARATUS FOR MEASURING PATIENT BLOOD LOSS

BACKGROUND OF THE INVENTION

This invention relates to a method and apparatus to improve an attending physician's or anesthesiologist's knowledge regarding the patient's status during and after a surgical procedure, and, consequently decreasing the risks to the patient stemming from that procedure. Specifically, the invention involves an apparatus capable of providing immediate information regarding a patient's cumulative blood loss during and after transurethral resection of the prostate, also called transurethral prostatectomy. The invention is also useful in the measurement of blood loss during and following a nephroscopy or a balloon dilation of the prostate.

All male humans have a prostate gland located just below the bladder. The prostate surrounds the urethra and produces seminal fluid. At puberty, the prostate is approximately the size of a chestnut. In many men, the prostate begins increasing in size around the fifth decade and gradually may reach the size of a baseball or even larger. Frequently, this growth is benign, although at times it is cancerous.

As the prostate grows larger, it squeezes inwardly around the urethra, narrowing it, and at times eventually leading to urinary retention in the bladder and to other complications.

Symptomatic growth or hypertrophy of the prostate is in general treated by removal of the excessive tissue growth by a surgical procedure called a prostatectomy. When the size, shape, and position of the enlarged prostate permit, a surgical procedure known as a transurethral resection (TUR) of the prostate is preferred. A TUR does not require an external incision, entails less blood loss, has fewer associated complications, and permits a shorter recovery period than an open prostatectomy.

A transurethral resection of the prostate is accomplished using an instrument called a resectoscope which is inserted through the urethra and which permits the physician to see inside the patient's urinary tract and to cut excess tissue using an electric loop extending from the resectoscope. The surgeon removes the obstructing tissue a piece at a time, and bits of tissue and accompanying blood are flushed out with a sterile irrigant which may enter and exit through a tube of the resectoscope. The removed tissue, associated blood and the flushing fluid are drained by tubing from the barrel of the resectoscope to a drain in the floor of the operating room.

In most patients, the transurethral resection of the prostate is carried out while the patient is anesthetized by spinal or epidural anesthesia. In managing patients undergoing such anesthesia, it is extremely helpful and important to the anesthesiologist to accurately know how much blood the individual patient has lost. It is also important to monitor a patient's blood loss following a transurethral resection to avoid post-operative complications. Blood loss during and following a transurethral resection of the prostate may, in extreme cases, vary from about thirty (30) milliliters to nineteen-hundred (1900) milliliters, and commonly varies from two-hundred (200) to eight-hundred (800) milliliters. At the present time no practical means is generally available for the anesthesiologist to continuously monitor a given patient's blood loss, since the volume of blood is intermixed with the volume of flushing fluid and drained into a drain in the operating room floor.

Simple expedients such as noting the drop in the level of the bottle of flushing fluid which feeds into the resectoscope, collecting the drained fluid and then estimating the difference in the two volumes to determine the blood loss, are inaccurate because of the absorption of fluid through venous channels at the surgical site. These methods are also inadvisable due to the possibility of the facilitation of bacterial contamination when the blood and flushing fluid are collected in a receptacle rather than drained away.

U.S. Pat. No. 4,562,842 discloses measuring apparatus for monitoring the loss of blood during a surgical procedure. The apparatus measures volume and weight of repetitive samplings of the mixture of blood and flushing fluid and then calculates the loss of blood based on known densities of blood and flushing fluid. The apparatus requires a reservoir to hold the blood/flushing fluid mixture while the necessary measurements of volume and weight are performed on volumes of the mixture withdrawn intermittently from the reservoir.

U.S. Pat. No. 4,575,240 discloses an apparatus for the spectrophotometric analysis of blood samples. The apparatus of the '240 patent is constructed such that blood samples can be analyzed automatically, but not continuously.

U.S. Pat. No. 4,357,105 discloses a high accuracy portable hemoglobinometer. The hemoglobinometer disclosed in the '105 patent utilizes spectrophotometric principles to determine the concentration of hemoglobin in properly prepared blood samples. One drawback of the hemoglobinometer of the '105 patent is that the hemoglobinometer does not analyze samples on a continuous basis.

U.S. Pat. No. 4,227,814 discloses an optical density detector for sensing the change in optical density of a fluid flowing through a flexible and light transmitting tube. The detector disclosed in the '814 patent is capable of continuously monitoring a flowing liquid through a clear and flexible tube. However, the detector is only capable of an on/off type analysis. It detects only the presence or absence of red blood cells in plasma flowing through the tubing of the detector, not relative amounts of red blood in the flushing fluid.

SUMMARY OF THE INVENTION

A principal object of this invention is to provide an apparatus for continuously determining the cumulative blood loss from a patient during a surgical procedure without collecting or interrupting the flow of a blood containing flushing fluid emanating from the patient.

Another object of this invention is to provide a method for monitoring the cumulative amount of blood lost from a patient during a surgical procedure.

Accordingly, in a broad embodiment the present invention is an apparatus comprising an outlet conduit means for conveying a blood containing liquid mixture from a surgical site during, or following a surgical procedure. The apparatus includes a first means for measuring the concentration of blood in the liquid mixture flowing through the outlet conduit means. The apparatus further comprises a second means for measuring the volumetric flow rate of the liquid mixture flowing through the outlet conduit means. Finally, the apparatus consists of a means responsive to both the first and second measuring means for calculating and displaying the cumulative amount of blood in the liquid mixture.

In a preferred embodiment, this invention is an apparatus for continuously calculating, updating and displaying the cumulative volume of blood lost from a patient as a result of a surgical procedure. The apparatus is useful in surgical procedures selected from the group consisting of a prostatectomy, a nephroscopy or a balloon dilation of the prostate The apparatus of this invention comprises:

a. an inlet conduit means for conveying a diluent to a surgical site and an outlet conduit means for removing a blood-containing liquid mixture comprising blood and a diluent from the surgical site;

b. a filter associated with the outlet conduit means for removing tissue and other solid matter from the blood-containing liquid mixture;

c. a spectrophotometer associated with the outlet conduit means for continuously measuring the concentration of blood in the blood-containing liquid mixture, the spectrophotometer capable of directing a first electric signal corresponding to the measured blood concentration to an electronic calculating means;

d. means associated with the outlet conduit means for continuously measuring the volumetric flow rate of the blood-containing liquid mixture removed from the surgical site, capable of directing a second electric signal corresponding to the volumetric flow rate to an electronic calculating means;

e. electronic calculating means capable of calculating a numerical value corresponding to the cumulative amount of blood in the blood-containing liquid mixture utilizing the first and second electric signals; and f. means electronically associated with the calculating means for observably displaying the numerical value corresponding to the cumulative amount of blood in the blood-containing liquid mixture.

Another object of this invention is to provide a method for continuously determining the cumulative amount of blood lost from a patient during or following a surgical procedure. The method includes the steps of optionally supplying a diluent solution to a surgical site, continuously or intermittently withdrawing a blood-containing liquid mixture from the surgical site, passing the blood-containing liquid mixture withdrawn from the surgical site through a filter, analyzing the blood-containing liquid mixture with a spectrophotometer after it has passed through a filter in order to determine the volumetric concentration of blood in the liquid mixture and generating a first electric signal corresponding to the concentration of blood in the blood-containing liquid mixture. The blood-containing liquid mixture is next passed through a flow meter to generate a second electric signal corresponding to the blood-containing liquid mixture volumetric flow rate. The first and second electric signals are combined in a signal processor and a numerical value corresponding to the cumulative amount of blood in the liquid mixture is electronically calculated and displayed. Finally, the liquid mixture is sent to a drain or other means of disposal.

DETAILED DESCRIPTION OF THE INVENTION

Figure 1:
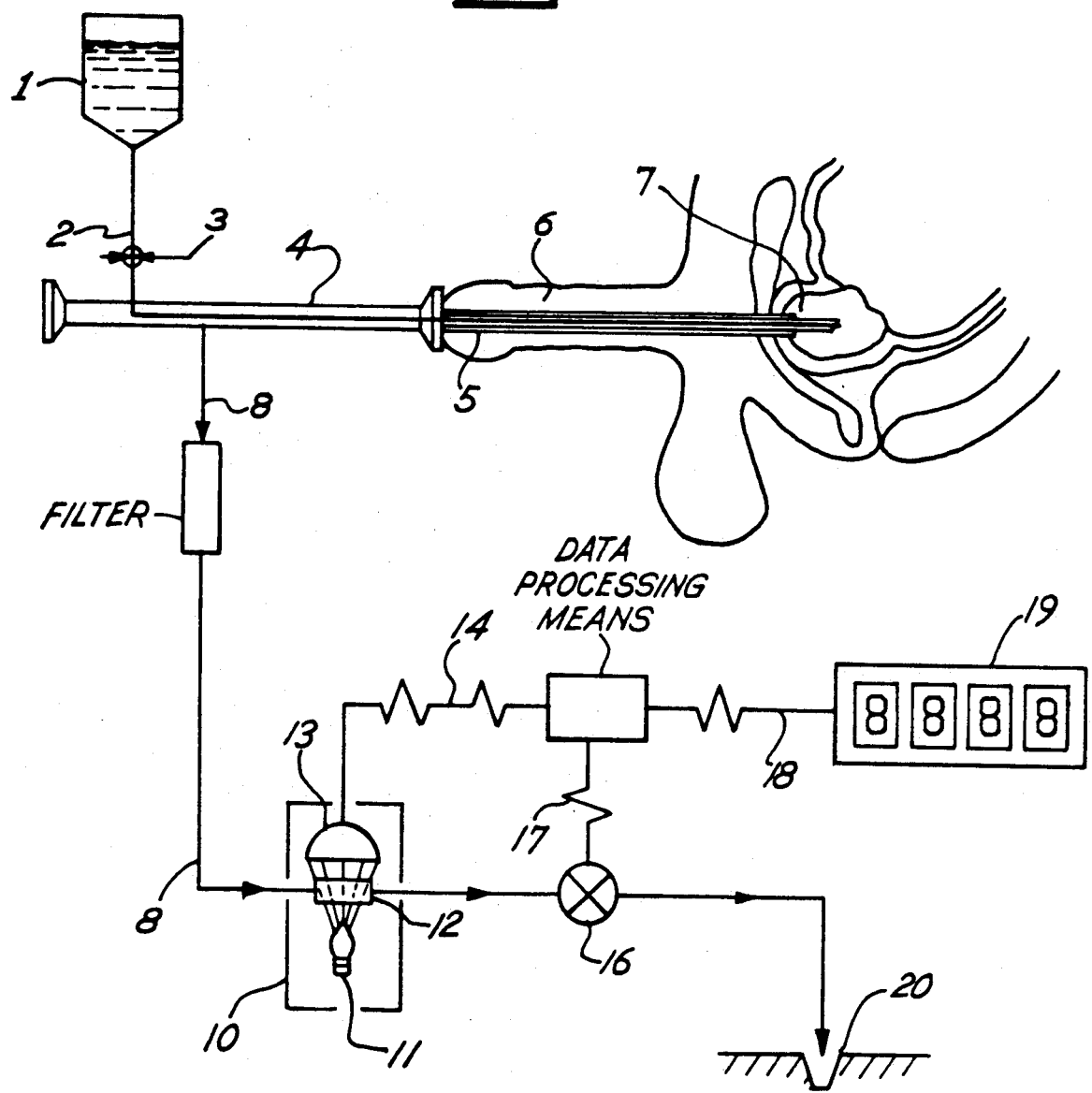
FIG. 1 represents a schematic diagram of the apparatus of this invention.

This invention is concerned primarily with an apparatus and method for measuring and displaying a patient's cumulative blood loss during surgery or during recovery from surgery, such that a surgeon or anesthesiologist may be continuously apprised of a patient's physiological status.

A great many surgical procedures result in a patient losing significant amounts of blood. The blood may be lost from a patient during the surgical procedure and/or soon after the surgical procedure while the patient is in the early stages of recovery. The apparatus and method of this invention are useful in measuring the cumulative amount of blood lost by a patient as a result of a surgical procedure. That is, the apparatus and method can be used to measure the amount of blood a patient loses during a surgical procedure, and while the patient is recovering from a surgical procedure.

It should be noted that the term surgical procedure is meant to connote the time period from the inception of the surgical procedure until the patient is no longer losing blood as a result of the surgical procedure. The term "surgical procedure" therefore encompasses post-operative patient blood loss monitoring.

Surgical procedures may be classified for purposes of this description as intrusive or alternatively non-intrusive. By intrusive it is meant that the surgical procedure includes steps of making incisions in the patient and performing the surgery while the surgical site is exposed to plain view. Alternatively, non-intrusive as the term is applied herein means surgery which typically utilizes a small incision or no incision at all on the exterior of the body. During non-intrusive surgery, an instrument of some kind is generally used to allow a surgeon to gain access to and view the surgical site. Non-intrusive surgery eliminates the necessity of exposing the surgical site to plain view. Examples of non-intrusive surgery include arthroscopic surgery and transurethral prostatectomies.

The apparatus and method of this invention are useful for determining the cumulative amount of blood lost by a patient as a result of either an intrusive or non-intrusive surgical procedure. It is preferred that the apparatus and method of this invention are used to measure the cumulative amount of blood lost by a patient as a result of a non-intrusive surgical procedure. The improved control of the flow of fluids to and from the site of a non-intrusive surgical procedure will likely result in better operation of the instant apparatus.

The apparatus and method of this invention are most useful for measuring the cumulative amount of blood in a liquid mixture withdrawn from a patient during and following surgical procedures. The apparatus of this invention is most useful when used in conjunction with surgical procedures such as a prostatectomy, (especially a transurethral resection), a nephroscopy, or a balloon dilation of the prostate.

The apparatus and method of this invention for measuring the cumulative amount of blood lost from a patient as the result of a surgical procedure are most useful in surgical procedures in which some sort of diluent is supplied to the surgical site, or where the diluent exists naturally at the surgical site, or both. Any diluent (non-blood liquid) present at the surgical site necessarily dilutes the amount of blood present. Additionally, in many surgical procedures, such as for example a TUR, the diluent solution might be adsorbed or enter the patient's blood stream or mingle with the patient's body fluids as a result of the pressure exerted by fluids at the non-intrusive surgical site. Finally, during a TUR procedure or immediately thereafter, urine may be commingled with any liquid mixture withdrawn from the surgical site. Therefore any liquid mixture withdrawn from the surgical site cannot be 100% blood. As a result, surgical blood loss cannot be directly measured by volume. Examples of diluents that might be supplied to the surgical site include, water, saline, and glycine solutions. Examples of natural diluents located in the area of a surgical site might include urine or other non-blood body fluids.

The rate of addition of the diluent solution to a surgical site will depend upon the particular surgical procedure being performed. When performing the preferred TUR, nephroscopy, or balloon dilation of the prostate, it is anticipated that about 3 liters to as much as about 40 to 50 liters of the diluent will be used over the course of the typical 45 to 90 minute surgical procedure. It is preferred that the diluent used during the surgical procedure is a glycine solution. It is preferred that a $H_2O$ or saline diluent is used following the surgical procedure.

The diluent may be supplied to the surgical site by any means known which enables the diluent to be utilized to irrigate and/or wash debris away from the surgical site. Normally the solution will be fed by gravity or by a small pump to the surgical site from a diluent reservoir. When performing a transurethral prostatectomy (TUR), a nephroscopy, or a balloon dilation of the prostate, it is preferred that any diluent be supplied by gravity to the surgical site. When performing a TUR the diluent is supplied by gravity to the surgical site using an instrument called a resectoscope.

The resectoscope comprises an inlet port by which a diluent can be introduced to the surgical site by the long tubular end of the resectoscope. The long tubular end of the resectoscope accesses the surgical site in the area of the bladder and prostate via a catheter inserted in the urethra. Typically the diluent solution will travel by gravity from a reservoir through an inlet conduit to the inlet port of the resectoscope. The diluent solution then passes through the long tubular end of the resectoscope where it is directed to the surgical site.

The resectoscope-catheter combination is also the preferred means by which a liquid mixture comprising blood, diluent solution and debris are removed from the TUR surgical site. The resectoscope-catheter combination form essentially concentric tubes, with the resectoscope tube being contained within the catheter tube. The resectoscope-catheter combination may be used to supply and/or withdraw the liquid mixture from the surgical site continuously or intermittently (batchwise). To intermittently withdraw a liquid mixture from the surgical site, the flow of diluent to the surgical site is first interrupted. The resectoscope is removed from the surgical site and withdrawn from the catheter. Finally, the liquid mixture is allowed to flow from the surgical site through the catheter connected to an outlet conduit means associated with measurement means discussed below. The resectoscope may then be reinserted into the catheter and exposed to the surgical site after the flow of the liquid mixture from the surgical site has subsided. At this point the diluent is again directed to the surgical site. This process can be repeated throughout the surgical procedure.

The resectoscope may also be used to supply a diluent to and simultaneously withdraw a liquid mixture from the surgical site. This is accomplished with a resectoscope having concentric tubing. The first concentric tube is used to supply the diluent solution to the surgical site. The second concentric tube is used to withdraw a liquid mixture from the surgical site. In this case, the resectoscope would still access the surgical site by being inserted in a catheter in the urethra.

The apparatus and method of this invention are both useful in measuring and monitoring post-operative blood loss from a patient during a surgical procedure. Typically, after a surgical procedure, such as a nephroscopy or a balloon dilation of the prostate, a patient will have a catheter installed to drain any liquid mixture that may accumulate at the surgical site. The liquid mixture flowing from the surgical site via a catheter or other means may be measured with the instant apparatus to determine a patient's post-operative cumulative blood loss.

The inlet and outlet conduit means used in the apparatus of this invention may be any known type of tubing or piping capable of transporting a liquid. However, due to the strict cleanliness standards utilized in hospitals, it is preferred that the conduit means be disposable plastic tubing.

The preferred apparatus as described thus far comprises a diluent reservoir connected by an inlet conduit means to the inlet port of a resectoscope. The resectoscope in combination with a catheter conveys the diluent solution by gravity to a surgical site A liquid mixture comprising blood may be intermittently or continuously withdrawn from the surgical site via an outlet conduit means.

The outlet conduit means first conveys the liquid mixture through a filter. The purpose of the filter is to remove debris such as blood clots and tissue washed away from the surgical site by the diluent solution. The filtering step produces a filtered liquid mixture. The filtering step is important as the flowmeter and spectrophotometer which subsequently measure particular properties of the liquid mixture may have their accuracy compromised if they encounter debris in the liquid mixture. The filter utilized may be most any type of filter capable of removing the large pieces of debris in the liquid mixture. It is preferred that the filter be a metal screen.

The filtered liquid mixture is conveyed by the outlet conduit means to either a flow meter or to a means for measuring the blood concentration of the liquid mixture. The order in which the liquid mixture encounters the two measuring means above is not believed to be critical and their position within the apparatus may be interchanged. For purposes of this disclosure, however, the means for measuring the blood content of the liquid mixture will be discussed first.

The outlet conduit means carries the filtered liquid mixture to a first means capable of measuring the concentration of blood in the liquid mixture. The first measuring means must be capable of supplying a first electric signal corresponding to the blood concentration of the liquid mixture to an information processing means.

The first measuring means may be any device capable of measuring or determining the blood concentration of the liquid mixture. It is preferred that the measuring means be a spectrophotometer. A spectrophotometer is an optical instrument that measures light energy transmitted through a solution or a gas at any given wavelength throughout the continuous band of wavelengths. The principal components of a spectrophotometer are a stable light source, monochromator (grating or prism), cuvet, adjustable slit, and energy detector.

To obtain measurements in the UV/visible range, an ordinary tungsten lamp may be used as the light source. For measurements in the UV region, mercury, hydrogen, or deuterium lamps are available.

The cuvet is a specimen holder. Typically a spectrophotometer measures discrete samples. However, the spectrophotometer utilized in the apparatus of this invention must continuously sample the liquid mixture stream passing through the outlet conduit means. Continuous sampling can be accomplished in a variety of ways. A preferred method of measuring blood concentration in the liquid mixture continuously is to analyze the liquid mixture blood concentration while it is flowing through the outlet conduit. This can be accomplished by utilizing a clear portion of conduit such as a glass section of outlet conduit or a transparent plastic section of outlet conduit at the point where the blood concentration of the liquid mixture is measured by the spectrophotometer. This can require that the side walls of the outlet conduit be planar at the sample detection point.

The spectrophotometer used will preferably operate with wavelengths of light corresponding to visible light. Visible light spectrophotometry is used both for the identification of chemical compounds by their characteristic absorption bands and for the determination of the concentrations of compounds by their absorbance at a particular wavelength, usually an absorption maximum. (By Beer's law absorbance is proportional to concentration.) The wavelengths most useful for determining the concentration of human hemoglobin (blood) in the liquid mixture are at about 560 nanometers and at about 430 nanometers.

The spectrophotometer utilized in the instant apparatus may be single-beam type instrument or a double-beam type instrument. In a single-beam instrument, only one light beam from source to detector is used. The meter measuring the current from the detector is adjusted to read zero (0) percent (Transmittance) with no light reaching the detector, and 100 percent T with a sample containing the reagent blank (which in this case would be the diluent solution) inserted in the light path. When measurements are made, the blank sample is replaced with one containing the liquid mixture, and the change in meter reading is noted. In a double-beam instrument, the light beam is split into two equal beams by a chopper or half-silvered mirror, with one beam passing through the reagent blank to its detector and the other through the specimen to its detector. The meter measures the difference in the current produced by the two beams, automatically compensating for variations in light source or detector response.

Finally, it is important that the spectrophotometer be able to continuously provide an electric signal known herein as the first electric signal, corresponding to the liquid mixture blood concentration, to an information processing means. In this manner, the information processing means can continuously determine the cumulative amount of blood that the patient has lost during the surgical procedure.

The outlet conduit means will also convey the liquid mixture through a flow measuring device. The flow measuring device or flow meter preferably measures the liquid mixture flow rate in units of volume or volume-per-unit of time. Types of flow meters useful for accurately measuring the volume-per-unit of time flow rate of a low flow rate stream include positive displacement flow meters, turbine type flow meters, magnetic flow meters and the like. The flow meter must be capable of accurately measuring a liquid flow rate ranging from about 5 to about 2000 cc/min. The flow meter used in the apparatus of this invention must also be capable of providing an electric signal referred to herein as the second electric signal, corresponding to the volume-per-unit of time flow rate of the liquid mixture, to a information processing means.

The information processing means of this invention must be capable of accepting the first electric signal from the spectrophotometer corresponding to the liquid mixture blood concentration and the second electric signal from the flow meter corresponding to the volume or volume-per-unit time flow rate of the liquid mixture. The information processing means then combines both electric signals to continuously calculate and update the cumulative volume of blood lost from the patient during the preferred surgical procedure. The information processing means will typically calculate the volume of blood in the liquid mixture for a known period of time, for example 10 seconds, by multiplying the value of the blood concentration of the liquid mixture during the period of time by the total liquid mixture flow rate for the same period of time. This will result in a number corresponding to the amount of blood leaving the surgical site for the particular known time period. This value will be added by the information processing means to all previous values of blood lost per unit of time to obtain an updated cumulative value of the total amount of blood the patient has lost during the surgical procedure or following the surgical procedure or both.

The information processing means will typically be electrically connected to a digital display means so that the amount of blood lost by the patient during or after the surgical procedure may be displayed. The digital display means will provide the anesthesiologist and/or surgeon with an essentially instantaneous readout of a value corresponding to the amount of blood the patient has lost during or after the surgical procedure. The display means electrically connected to the information processing means may be a digital LED, LCD or a mechanical display. It is preferred that the display indicates the cumulative amount of blood lost in grams of hemoglobin.

After conveying the liquid mixture to the blood concentration measuring means and the flow measuring means, the outlet conduit means directs the liquid mixture to a liquid mixture disposal means. Such a disposal means is typically a floor drain or discrete conduit for carrying the liquid mixture away from the surgical arena or recovery room.

The apparatus of this invention is further understood by reference to FIG. 1.

FIG. 1 is a schematic diagram depicting the apparatus of this invention as it would be used during a transurethral resection. The apparatus comprises a diluent solution reservoir 1 which contains a diluent solution such as a glycine solution. The diluent solution passes through inlet conduit 2 to a resectoscope 4. The flow of the diluent solution may be started or stopped by means of valve 3. The resectoscope 4 is placed in a tube or catheter 5 which is inserted into the urethra 6. The resectoscope 4 extends through the catheter at a length sufficient to bring it into contact with the prostate 7.

Typically during the TUR procedure the diluent solution is allowed to flow to the surgical site by gravity until pressure at the surgical site caused by fluid accumulation causes the diluent solution to stop flowing. At this point the diluent solution flow is stopped by closing valve 3 and the resectoscope 4 is removed from the catheter 5. The liquid mixture located at the surgical site is then allowed to flow through the catheter 5, to an outlet conduit 8 and through a filter. The filter removes debris such as bits of tissue and blood clots from the liquid mixture. Alternatively, and as depicted in FIG. 1, the liquid mixture may be continuously withdrawn from the surgical site using outlet conduit 8 which is attached to the resectoscope 4.

Figure 1A:
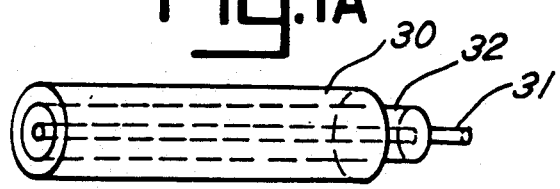
FIG. 1A shows a blow up view of a cross section of the preferred resectoscope-catheter combination of this invention.

The ability of the resectoscope 4 to continuously withdraw a liquid mixture from a surgical site is better understood by reference to FIG. 1A. FIG. 1A is a blow-up view of a cross section of a resectoscope contained within a catheter 30. The catheter 30 encloses the resectoscope barrel comprising a first concentric tube 31 for supplying a diluent to the surgical site and a second concentric tube 32 for withdrawing a liquid mixture from the surgical site.

Returning to FIG. 1, the filtered liquid mixture continues to flow through the outlet conduit 8 to be continuously analyzed by the spectrophotometer 10. The spectrophotometer 10 comprises a light source 11 which directs a beam of light through a transparent conduit portion 12 of the outlet conduit 8. The intensity of light passing through the liquid mixture in the transparent portion 12 is measured by a detector 13. The detector 13 measures the amount of light of a specific wavelength (usually about 430 or about 560 nanometers) not absorbed by hemoglobin in the liquid mixture. The amount of light detected corresponds to the liquid mixture hemoglobin or blood concentration. A first electric signal 14 corresponding to the hemoglobin concentration of the flowing liquid mixture is relayed from the detector 13 to an data processing means.

The liquid mixture is ext passed through outlet conduit 8 to a flow meter 16 in order that the liquid mixture flow rate may be determined. A second electric signal 17 corresponding to the liquid mixture flow rate is relayed to the data processing means from the flow meter 16. The data processing means calculates the cumulative blood volume in the liquid mixture and sends a third electric signal 18 corresponding to the cumulative blood volume to a digital display means 19 which constantly and visibly indicates a numerical value corresponding to the amount of blood lost from the patient in grams of hemoglobin. Finally, the liquid mixture is directed to a floor drain 20.

While the preferred embodiment of the invention has been described and potential modifications suggested, it should be understood that other embodiments could be devised based on the operating principal of the apparatus and method of this invention which would remain within the spirit of the invention and the scope of the appended claims.

What I claim is:

1. An apparatus for continuously monitoring a cumulative volume of blood in a blood-containing liquid mixture emanating from a patient as a result of a surgical procedure, said apparatus comprising:
   (a) an outlet conduit means for conveying the liquid mixture comprising blood from a surgical site;
   (b) a filter means for filtering the liquid mixture to define a filtered liquid mixture;
   (c) first means for measuring the concentration of blood in the filtered liquid mixture;
   (d) second means for measuring the volumetric flow rate of the filtered liquid mixture; and
   (c) means responsive to said first and said second measuring means for calculating and means for displaying the cumulative volume of blood flowing from the surgical site.

2. The apparatus of claim 1 wherein the first means for measuring the concentration of blood in the liquid mixture comprises a spectrophotometer.

3. The apparatus of claim 1 wherein the cumulative volume of blood flowing through the conduit means is displayed in units of weight.

4. The apparatus of claim 1 wherein the outlet conduit means comprises clear plastic tubing.

5. The apparatus of claim 1 wherein the liquid mixture further comprises urine, or a diluent or mixtures thereof.

6. An apparatus for continuously monitoring and displaying a cumulative volume of blood lost from a patient as a result of a surgical procedure selected from the group consisting of a prostatectomy, a nephroscopy, or a balloon dilation of the prostate which comprises:
   (a) an outlet conduit means for removing a liquid mixture from a surgical site;
   (b) a filter means associated with the outlet conduit means for removing debris from the liquid mixture to define a filtered liquid mixture;
   (c) a spectrophotometer associated with the filter means for continuously measuring the concentration of blood in the filtered liquid mixture, said spectrophotometer providing a first electric signal corresponding to the measured blood concentration;
   (d) flow measuring means associated with the filter means for continuously measuring the volumetric flow rate of the filtered liquid mixture removed from the surgical site, said flow measuring means providing a second electrical signal corresponding to the liquid mixture volumetric flow rate;
   (c) means for electronically calculating a numerical value corresponding to the cumulative volume of blood in the filtered liquid mixture from the first and second electric signals; and
   (f) means for displaying said numerical value corresponding to the cumulative volume of blood in the filtered mixture.

7. The apparatus of claim 6 wherein the cumulative volume of blood in the filtered liquid mixture is calculated and displayed in units of weight.

8. The apparatus of claim 6 wherein the spectrophotometer comprises a light source and a detection means for measuring a wavelength of light which corresponds to a wavelength absorbed by human hemoglobin.

9. The apparatus of claim 6 wherein said outlet conduit means comprises a resectoscope and a catheter and wherein said resectoscope in conjunction with said catheter supplies a diluent solution to and removes the liquid mixture from the prostatectomy site.

10. The apparatus of claim 6 wherein the outlet conduit means is transparent and wherein the spectrophotometer analyzes blood concentrations of the filtered liquid mixture.

11. A method for continuously monitoring a cumulative volume of blood lost from a patient as a result of a surgical procedure comprising the steps of:
   (a) supplying a diluent to a surgical site;

(b) withdrawing a liquid mixture comprising said diluent, blood and body fluids from the surgical site;
(c) passing the liquid mixture through a filter to define a filtered liquid mixture;
(d) analyzing the filtered liquid mixture with a spectrophotometer to determine the volumetric concentration of blood in the filtered liquid mixture, and generating a first electric signal corresponding to the blood concentration;
(e) passing the filtered liquid mixture through a flow meter to generate a second electric signal corresponding to the filtered liquid mixture flow rate;
(f) generating a display corresponding to the cumulative volume of blood in the filtered liquid mixture by directing the first and second electric signals of steps (d) and (e) to a signal processor and electronically calculating and continuously displaying the cumulative volume of blood in the filtered liquid mixture in grams; and
(g) disposing of the filtered liquid mixture.

12. The method of claim 11 wherein the surgical procedure is a prostatectomy, a nephroscopy, or a balloon dilation of the prostate.

13. The method of claim 12 wherein the surgical procedure is a prostatectomy and in that a resectoscope in combination with a catheter is used both to supply the diluent to the surgical site and to withdraw the liquid mixture from the surgical site.

14. The method of claim 13 wherein the liquid mixture is removed from the surgical site batchwise.

15. The method of claim 13 wherein the liquid mixture is continuously removed from the surgical site.

16. The method of claim 11 wherein the spectrophotometer detects light at a wavelength of 430 and 560 nanometers.

17. The method of claim 11 wherein the cumulative volume of blood in the liquid mixture is calculated and displayed in units of volume.

* * * * *